United States Patent [19]
Orth et al.

[11] Patent Number: 5,836,913
[45] Date of Patent: Nov. 17, 1998

[54] DEVICE AND METHOD FOR ACCESSING A BODY CAVITY

[75] Inventors: Michael J. Orth, Morgan Hill; John E. Carlson, San Jose; William R. Dubrul, Redwood City; Steven P. Masterson, San Francisco, all of Calif.

[73] Assignee: Innerdyne, Inc., Sunnyvale, Calif.

[21] Appl. No.: 850,795

[22] Filed: May 2, 1997

[51] Int. Cl.⁶ .................................................. A61M 37/00
[52] U.S. Cl. ............................................ 604/107; 604/174
[58] Field of Search ................................... 604/93, 96, 97, 604/98, 99, 101, 102, 104, 105, 106, 107, 108, 109, 174, 175

[56] References Cited

U.S. PATENT DOCUMENTS

| | | | |
|---|---|---|---|
| 3,915,171 | 10/1975 | Shermeta | 604/101 |
| 4,496,345 | 1/1985 | Hasson | 604/103 |
| 4,617,933 | 10/1986 | Hasson | 128/348 |
| 5,002,557 | 3/1991 | Hasson | 604/174 |
| 5,041,093 | 8/1991 | Chu | 604/104 |
| 5,176,697 | 1/1993 | Hasson et al. | 606/191 |
| 5,188,602 | 2/1993 | Nichols | 604/107 |
| 5,209,754 | 5/1993 | Ahluwalia | 606/119 |
| 5,267,970 | 12/1993 | Chin et al. | 604/175 |
| 5,344,439 | 9/1994 | Otten | 604/107 |
| 5,421,832 | 6/1995 | Lefebvre | 604/107 |
| 5,454,790 | 10/1995 | Dubrul | 604/104 |
| 5,540,658 | 7/1996 | Evans et al. | 604/101 |

*Primary Examiner*—Max Hindenburg
*Attorney, Agent, or Firm*—Townsend and Townsend and Crew LLP

[57] ABSTRACT

Devices and methods for providing access to a body cavity without substantial loss of inflation gas therein. The device comprises an access assembly 10 that may have a tubular member 12, at least one sleeve 16 coaxially disposed over the tubular member, a pneumostasis valve 13 attached to the tubular member, and an obturator 11 removably received in the tubular member. Sleeve 16 comprises expandable region 19 capable of forming an anchor 30 upon axial compression. A method to provide access using assembly 10 comprises insertion of the assembly 10 into the body cavity, expanding region 19, and insufflating the cavity with gas. Expandable region 19 on assembly 10 is axially compressed to form anchor 30 to seal against an interior wall of the body cavity. The method may further comprise either a second expanded anchor 50 or a non-expanding anchor 40 which clamps against an exterior wall of the body cavity to securely position and seal the access assembly 10.

21 Claims, 7 Drawing Sheets

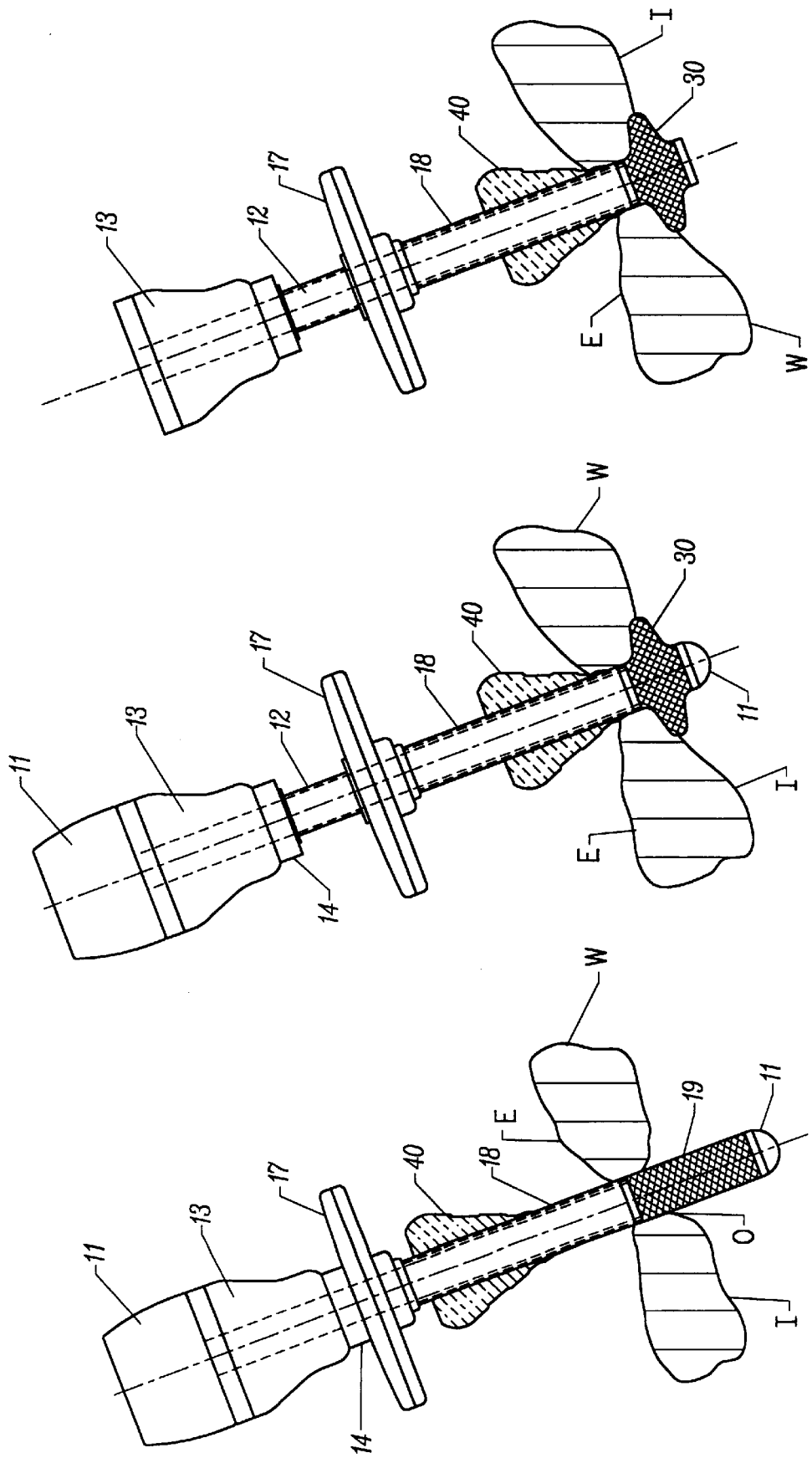

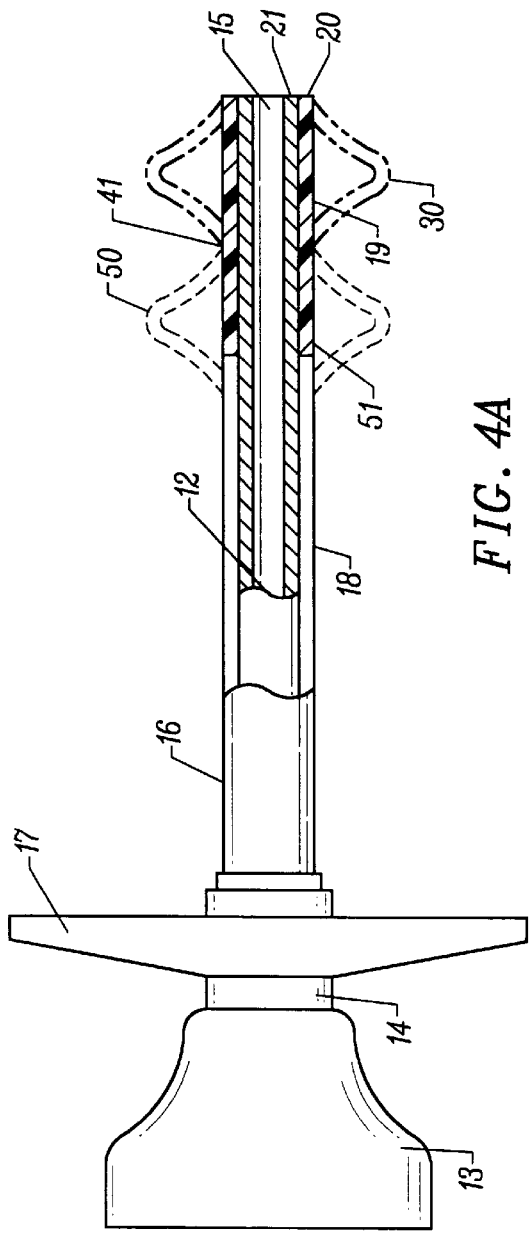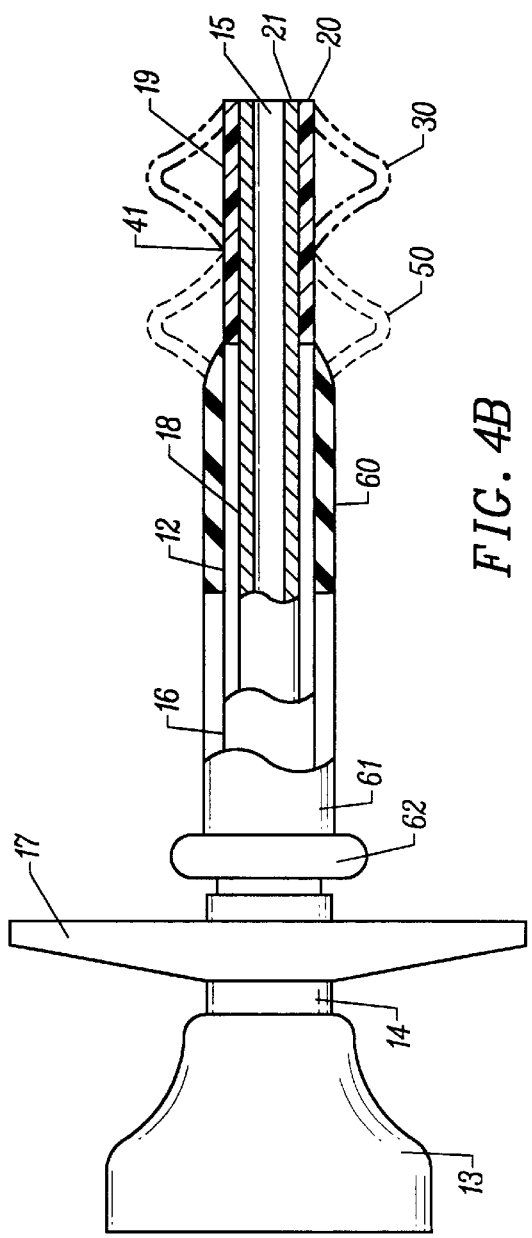
FIG. 4A
FIG. 4B

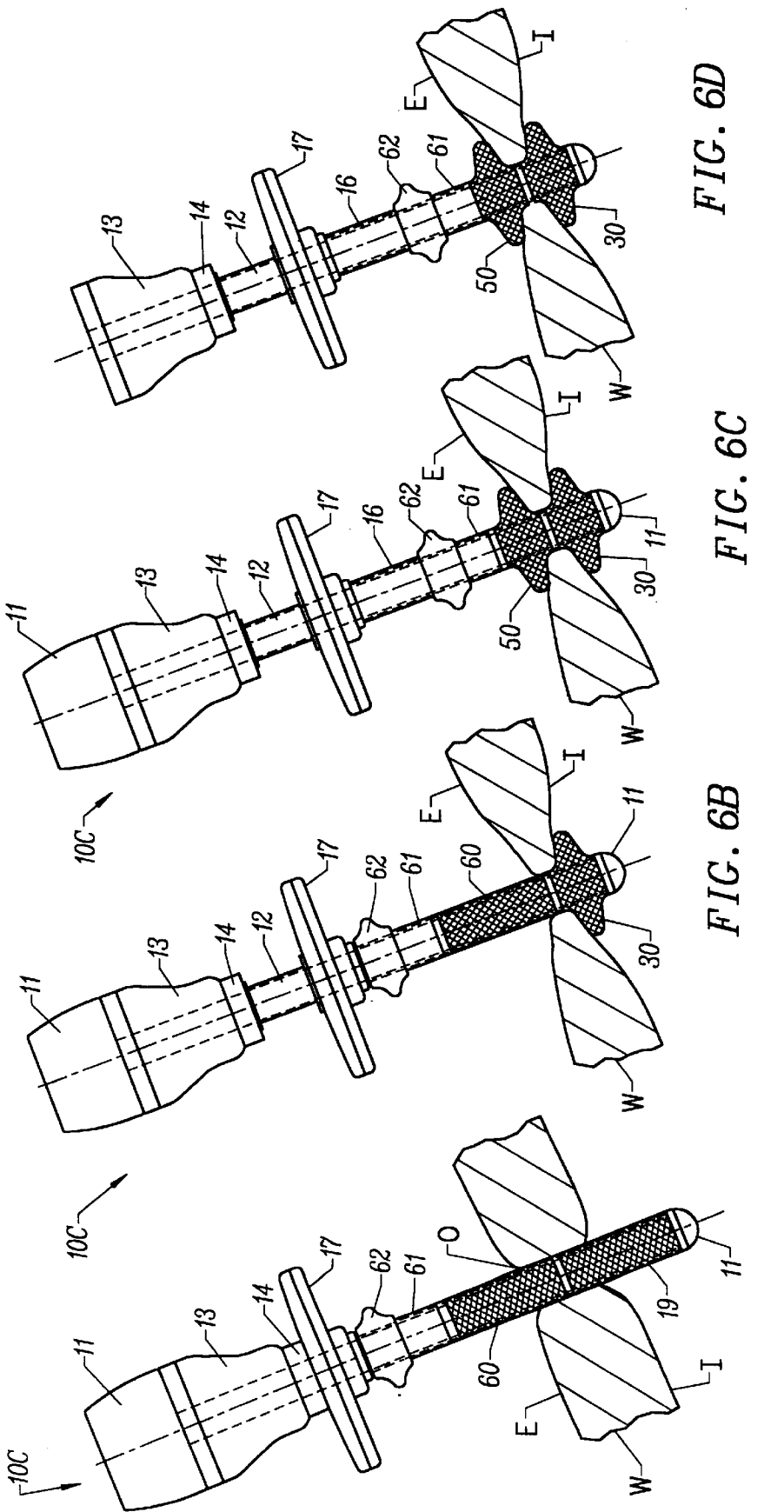

DEVICE AND METHOD FOR ACCESSING A BODY CAVITY

BACKGROUND OF THE INVENTION

1. Field of the Invention

The present invention relates generally to devices and methods for introducing medical instruments into the abdomen. In particular, the present invention relates to an abdominal access assembly having an expandable anchor to secure and seal the access assembly to the abdominal wall of the patient.

"Minimally invasive" surgical procedures have recently been developed as alternatives to conventional "open" surgery. Minimally invasive procedures, such as laparoscopy, involve accessing the surgical area inside a patient through a plurality of ports created in the patient's body. This type of procedure is generally less traumatic to the body than open surgery and since these ports tend to cause less tissue damage and blood loss as compared to cuts made on the body for open surgery. To provide space inside the surgical area for instruments to operate, the abdominal wall must be elevated from the organs in the intra-abdominal cavity for typical endoscopic or laparoscopic procedures. This is usually accomplished by filling the cavity with a gas, such as carbon dioxide, to inflate the cavity. This process, known as insufflation, is typically achieved by inserting a large-gauge needle known as a Veress needle into the intra-abdominal cavity for the introduction of gas. To perform surgical procedures in the intra-abdominal cavity, the insufflation must be maintained, as the abdominal wall must remain elevated from the organs in the intra-abdominal cavity.

Once enlarged, the cavity is accessed by inserting a trocar and cannula assembly through the abdominal wall. The trocar is sharp stylet used to provide an initial penetration and access opening in the abdominal wall for the cannula. Introduction of the trocar can present significant risk to the patient, especially the first opening which is performed blind, i.e. prior to introduction of the laparoscope. The risks stem from possible excessive penetration by the trocar causing injury to underlying internal organs. The risk is exacerbated by the toughness and elasticity of the abdominal wall which require substantial manual force for trocar penetration.

To reduce the risks of organ penetration, an alternative method known as the "open laparoscopy" method or the Hasson method exists for establishing access openings without the use of a sharp trocar. In accordance with this method, access can be established to the peritoneal cavity through a small incision on the skin of the abdomen, typically through the umbilicus. Continuous visual control is maintained for insertion of a special open laparoscopic cannula. The physician uses standard laparotomy instruments and grasping forceps to laterally enlarge the initial incision and to lift/separate the fascia. This procedure eventually exposes the peritoneum and places it under tension so that it can be carefully pierced. Once accessed, the physician can pass a gloved finger into the cavity accessing the relevant anatomy and confirming safe entry. Upon securing safe access, the physician can insert the cannula with a blunt dilator through the mini-laparotomy and continue with a standard laparoscopic procedure.

During the surgical procedure, the pressurized integrity of the peritoneal cavity or pneumoperitoneum must be maintained even though there is substantial movement of the cannula directed by the needs of the surgery. Unfortunately, it is often difficult to maintain a proper seal between the cannula and body tissue at the initial incision point. Prior art devices have typically employed a conical shaped sealing anchor generally constructed from a rigid material. Upon insertion into the incision, the sleeve's conical geometry pushes or displaces outward the tissue surrounding the incision. The tissue's natural resiliency will then cause the tissue to try to return to the tissue's original position which creates a sealing force against the surface of the sealing sleeve. The cone is usually sutured to the skin at a depth and position where the tissue's resiliency provides sufficient compression to maintain a seal. The cone may be anchored to the skin by other devices such as adhesives, skin staples or spring clips. Another device to maintain the integrity of the gas seal employs an inflatable membrane at the insertable end of the cannula and securely positions the cannula by capturing a patient's tissue between a sealing sleeve and the inflatable membrane.

Unfortunately, these devices have drawbacks. Connecting the anchor to the skin through suturing or other external means adds unnecessary trauma and complication to the procedure. These cone anchoring devices themselves add additional moving parts which complicates the device. The inflatable balloon-like anchor can rupture through contact with sharp surgical instruments, causing a catastrophic loss of pneumoperitoneum and subsequent loss of visualization from the resulting collapse.

2. Description of the Background Art

U.S. Pat. Nos. 5,002,557 and 5,176,697 disclose a laparoscopic cannula having an inflatable anchor. U.S. Pat. Nos. 4,496,345; 5,209,754; and 5,540,658 show transcervical devices having expandable anchors for either maneuvering or securing the uterus. A device for mounting a cannula to a body of a patient is disclosed in U.S. Pat. No. 5,267,970. U.S. Pat. No. 4,617,933 shows a laparoscope cannula with improved suture receiving means. A cannula having a Malecot structure at a distal end of the cannula to prevent retraction is described in U.S. Pat. No. 5,454,790.

SUMMARY OF THE INVENTION

The present invention is directed at devices and methods capable of providing a gas seal against a penetration in the abdominal wall without the use of suturing, external adhesive devices, or an inflatable anchor. The device of the present invention generally has an expandable anchor designed to prevent withdrawal of an abdominal access device such as a cannula while maintaining pneumoperitoneum in the abdominal cavity. The anchor is integrated into the device design, will not rupture, and does not traumatize the body tissue against which it anchors.

In a basic embodiment, the device of the present invention is an abdominal access assembly comprising a tubular member, a first sleeve, a pneumostasis valve, and a blunt obturator. The tubular member has a proximal end, a distal end, and a lumen therethrough. The first sleeve is disposed coaxially over the tubular member and has a distal radially expandable region and a proximal non-expandable region. The sleeve shifts over the tubular member between either an axially elongated configuration where the sleeve's distal region is unexpanded and an axially shortened configuration where the sleeve's distal region is radially expanded. Both the pneumostasis valve and the obturator are in contact with the tubular member. The valve is attached to the proximal end of the member, and the obturator is removably received in the lumen of the tubular member.

In a specific embodiment, the assembly operates in conjunction with a sealing anchor slidably mounted over the proximal non-expandable region of the sleeve, wherein the sealing anchor can be advanced toward the radially expanded, expandable region to clamp a patient's abdominal tissue. The anchor may have a conical configuration. Advancing the anchor in the proximal direction towards the expanded distal, expandable region, bring the two together, defines a neck having opposed tapered walls between which the abdominal wall may be clamped.

In an exemplary embodiment of the assembly, the sleeve of the device has an intermediate radially expandable region and a distal radially expandable region. The sleeve shifts over the tubular member between an axially elongated configuration where both the distal and the intermediate regions are unexpanded and an axially shortened configuration where both the distal and the intermediate regions are radially expanded. In this embodiment, the states of both expandable regions are coupled together.

In a still further embodiment, the assembly has first and second sleeves with the second sleeve coaxially disposed over the proximal non-expandable region of said first sleeve. The second sleeve has a distal, a proximal end, and an intermediate radially expandable region. This embodiment focuses on decoupling the two expandable regions, by allowing one to expand while the other does not.

The expandable regions of the present invention generally comprise a non-distensible imperforate cylinder. In a specific aspect, the region is essentially a radially expandable mesh covered with an elastomer sheath.

The assembly of the present invention may also have a length of the tubular member extending beyond the distal end of the first sleeve. This provides a certain amount of flexibility as to the length of the assembly protruding into a body cavity. Such length adjustability may also be achieved by adding a cannula slidably and concentrically disposed within the tubular member of the assembly.

A method of the present invention for providing access to a patient's abdomen includes the method step of introducing a tubular body through a penetration in the patient's abdomen. In specific aspects, the penetration occurs through the umbilicus of the patient. A radially expandable member mounted on the tubular body is axially compressed to radially expand the member. This expansion provides a seal against the internal surface of an abdominal wall. The abdomen is insufflated with a gas to provide space in the abdomen for surgical instruments. The seal created by the expandable region inhibits loss of the gas through the penetration.

In certain embodiments, a proximal anchor on the tubular body may be advanced to clamp against the abdominal wall. In exemplary embodiments, the tubular body has a distal and an intermediate expandable body, both of which are compressed to radially expand the regions to clamp an abdominal wall therebetween. The distal region provides a seal against the internal surface of an abdominal wall to prevent the loss of insufflation gas.

These and other embodiments of the present invention, as well as its advantages and features, are described in more detail in conjunction with the text below and attached figures.

BRIEF DESCRIPTION OF THE DRAWINGS

FIGS. 3A–3C depict a method of the present invention using the assembly of FIGS. 2A–2C and a non-expandable sealing anchor.

FIG. 4A shows a cross-section of the assembly having coupled anchors.

FIG. 4B shows a cross-section of the assembly having decoupled anchors.

FIGS. 6A–6D depicts a method of the present invention using the assembly of FIG. 4B.

DETAILED DESCRIPTION OF THE SPECIFIC EMBODIMENTS

Methods and apparatus of the present invention are directed towards providing access to a gas containing body cavity without substantial loss of gas from the body during surgical procedures. Specifically, the invention prevents substantial loss of pneumoperitoneum through a penetration in the abdominal wall by providing an access assembly that can form a peripheral seal against the penetration while allowing surgical instruments to access the abdomen during minimally invasive surgical procedures.

To reach a desired body cavity, the access assembly is inserted through a percutaneous opening in the patient's abdomen. In preferred embodiments, the opening occurs through the umbilicus of the patient. The access assembly must typically pass through the abdominal wall which includes the outer skin, a layer of fat, a layer of fascia or alternating muscle and fascia, and the peritoneum. The layers of fat and fascia may vary in thickness, depending upon the body location and whether the patient is asthenic or obese. The peritoneum is a strong, elastic membrane lining the walls of the abdominal cavity. Just below the peritoneum, lie several vital organs, such as the liver, stomach and intestines, and other sensitive tissues. This is typically the area that the access assembly is positioned to reach.

To perform surgical procedures in this area, the abdominal wall is lifted off of the organs by inflating the area with an insufflation gas such as carbon dioxide. This provides sufficient space for surgical instruments to maneuver. To prevent loss of this gas and loss of space in the abdomen to operate, the access assembly must provide a gas-tight seal against the abdominal wall while permitting a sufficient range of motion for the instruments and not traumatizing the portion of the abdominal wall in the seal.

Figure 1A:
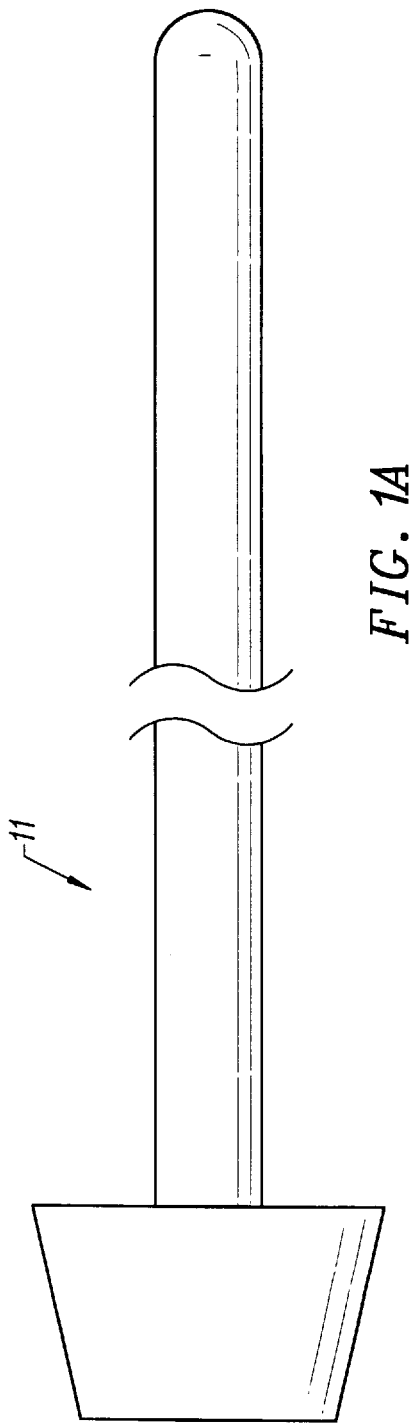
FIG. 1A illustrates a blunt obturator of the access assembly.
Figure 1B:
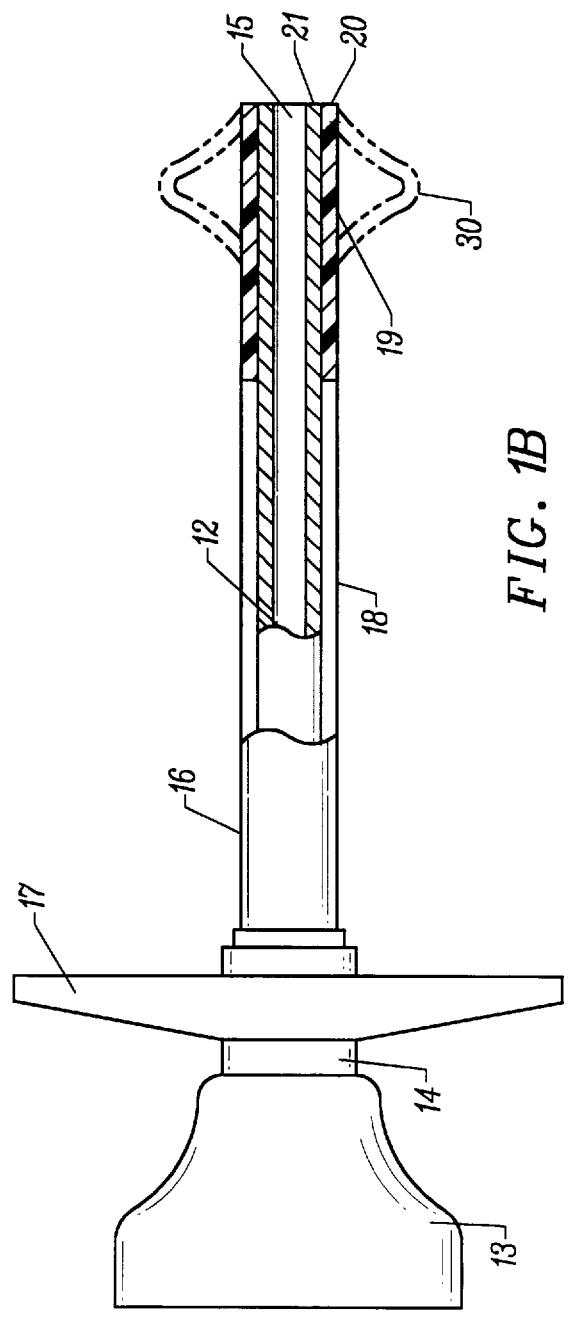
FIG. 1B shows a side-view of the access assembly with the obturator removed.

In a basic embodiment, the abdominal access assembly 10 of the present invention (see FIG. 2) generally comprises a blunt obturator 11 (FIG. 1A) and a tubular member 12 (FIG. 1B) having a pneumostasis valve 13 fitted to the proximal end 14 of the tubular member 12. The blunt obturator 11 slides removably into a lumen 15 of the tubular member 12 through pneumostasis valve 13 and proximal end 14 of the tubular member 12. Although a blunt obturator 11 is preferred, a variety of other instruments may also be inserted into the lumen 15 so long as they facilitate atraumatic insertion of the access assembly 10 into a body cavity of the patient. The pneumostasis valve 13 may be housed inside a hub attached to the tubular member 12. The valve 13 may be a flap valve or a gas-restricting device of some other design, so long as it allows entry of a surgical instrument while minimizing substantial loss of insufflation gas during the surgical procedure.

To form a peripheral seal between the access assembly 10 and a percutaneous opening in the abdominal wall, the assembly 10 has a first sleeve 16 disposed coaxially over the tubular member 12. The sleeve 16 is connected to a handle 17 and both slide over the tubular member 12. The sleeve 16 comprises a proximal nonexpandable region 18 and a distal expandable region 19 (see FIG. 2). End 20 on the expandable region 19 is connected to distal end 21 on the tubular member 12 so that the sleeve 16 can slide over but not detach from tubular member 12. The handle 17 is used to axially translate the sleeve 16 which results in the compression of region 19. The distal expandable region 19 expands radially when axially compressed to form distal expanded occlusion member or anchor 30. As will be discussed below, the expanded anchor 30 forms a peripheral seal to prevent the loss of gas from the body cavity.

To axially translate the sleeve 16 over the tubular member 12, a variety of mechanisms can be employed such as using a pistol grip advancing system or some other translating mechanism. All must, however, effectuate axial compression of the distal expandable region 19. A convenient way to axially compress the distal expandable region 19 is to prevent axial movement of the tubular member 12 and the distal end of region 19 while axially advancing the sleeve 16 in the distal direction. An exemplary mechanism for axially translating the sleeve 16 relative to the tubular member 12 is handle 17 as shown in FIGS. 1–6.

In a specific aspect of the present invention for forming a peripheral seal, the distal expandable region 19 of sleeve 16 is a non-distensible imperforate cylindrical surface preferably constructed from an elastomeric sheet covering a mesh or braided material, as shown in the figures. Specific methods for forming and details regarding the elastomeric sheet and the mesh are described in commonly assigned U.S. Pat. No. 5,540,658 to Evans et al., the complete disclosure of which is incorporated herein by reference. Exemplary materials for the mesh or braided material include polymer strands such as PET, polypropylene, polyethylene, and the like. Exemplary materials for the elastomeric sheet include latex, silicone, thermoplastic elastomers (such as C-Flex, commercially available from Consolidated Polymer Technology), and the like. The mesh is formed into a cylindrical geometry and, as mentioned, is translatably disposed over tubular member 12. The distal ends of both the mesh and sheet are attached to the distal end 21 of tubular member 12 so that when the expandable region 19 is axially compressed, the expandable region 19 will both axially compress and radially expand to form the distal expanded anchor 30. To ensure that the expandable region 19 will radially expand to the desired configuration, the mesh can be pre-fatigued, heat forged or bonded in preselected locations, e.g., along a circumferential line. When the mesh is axially compressed, the mesh will radially expand about the line.

In an exemplary aspect, the mesh can also be used to form the tubular body 12 by proximally extending the mesh from the expandable region 19. A cover tube can be placed over the extended mesh so that the exterior surface of the tubular body 12 is substantially flush with the expandable region 19. An exemplary material for constructing the cover tube is a cross linked heat shrink polymer. In this manner, the expandable region 19 can be made to closely conform to the exterior of the tubular member 12.

The tubular member 12 can be constructed from a variety of materials including stainless steel, composite filament wound polymer, or extruded polymer tubing (such as Nylon 11 or Ultem, commercially available from General Electric), and the like. These materials have sufficient strength so that the tubular body 12 will not collapse when inserted into the abdomen or when the distal expandable region 19 is compressed. Although specific dimension vary depending on the surgical procedure, the tubular member 12 has an outer diameter from about 4 mm to 20 mm and a length between about 5 cm and 15 cm.

Figure 2A:
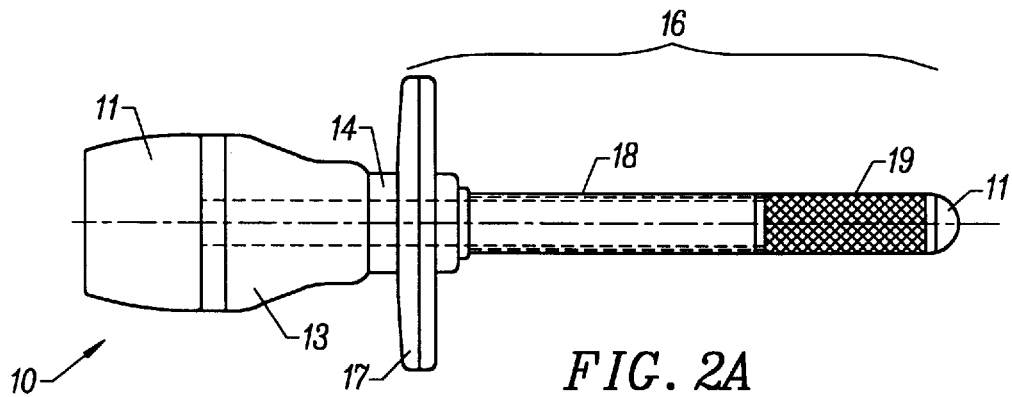
FIGS. 2A–2C show side-views of one embodiment of the access assembly having a single anchor.
Figure 2B:
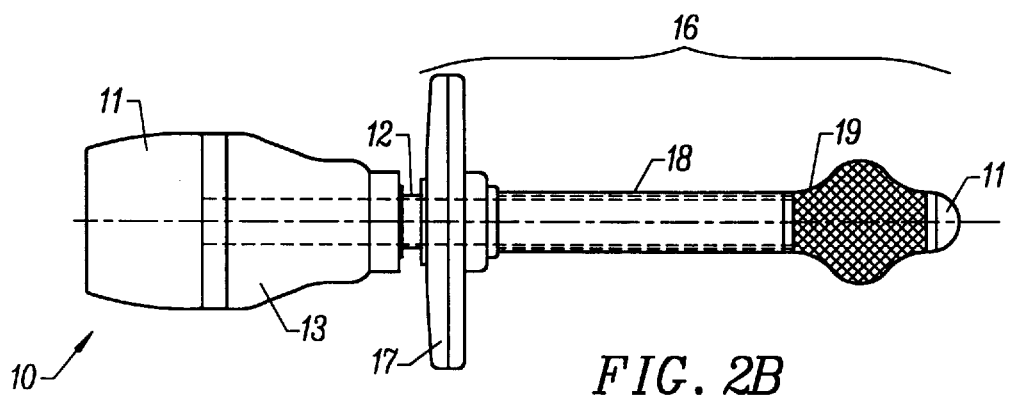
Figure 2C:
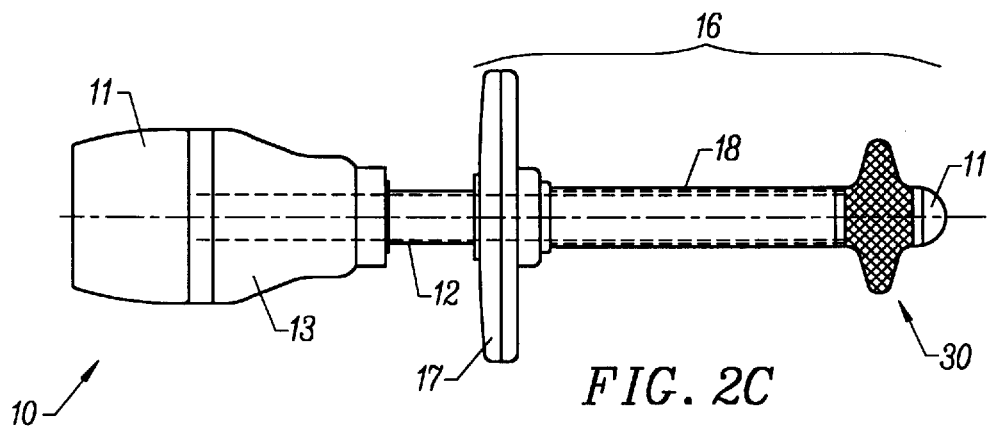

Referring to FIGS. 2–3, access assembly 10 is shown fully assembled with the blunt obturator 11 inserted into the tubular member 12. FIG. 2A–2C shows an access assembly 10 capable of forming a single expanded anchor 30. As the sleeve 16 is axially translated towards a distal end of the tubular member 12 in FIG. 2B, the expandable region 19 compresses to cause radial expansion. In FIG. 2C, the region 19 has reached maximum radial expansion and forms the single anchor 30. The anchor 30 generally assumes a conical configuration which diverges in the distal direction when axially compressed. Preferably, the maximum outer diameter of the distal anchor 30 will be in the range from about 10 mm to 50 mm.

FIGS. 3A–3C depicts an alternate embodiment of the present invention and a method for the present invention. The device of FIGS. 3A–3C is essentially the assembly 10 of FIGS. 2A–2C further comprising a non-expanding sealing anchor 40 sliding coaxially over sleeve 16. The non-expanding anchor 40 is typically a cone structure which diverges in the proximal direction. The expanded anchor 30 and non-expanding anchor 40 will slide to clamp around abdominal wall W to form a peripheral seal.

The method of the present invention as illustrated in FIG. 3A shows access assembly 10 inserted into a percutaneous opening O made in abdominal wall W. Preferably, the opening O was made using the Hasson method, which avoids the use of a trocar and reduces risk for organ puncture. The blunt obturator 11 helps the assembly push aside tissue without trauma. The access assembly 10 is positioned at a depth so that distal expandable region 19 will form the anchor 30 on the interior side I of abdominal wall W.

FIG. 3B shows the anchor 30 forming a seal against the interior side I of the abdominal wall W. The sleeve 16 has translated axially towards the distal end and has compressed region 19 to form anchor 30. Non-expanding anchor 40 is advanced axially towards the distal end of the tubular member 12 to form a reduced diameter neck with anchor 30. The non-expanding anchor seals against the interior of opening O and the exterior surface E of the abdominal wall W. The anchors 30 and 40 clamp around the abdominal wall W to prevent retraction of the assembly 10 and also to prevent loss of pneumoperitoneum from the abdomen. After the access assembly 10 is secured and peripherally sealed to the puncture, the blunt obturator 11 is removed from the tubular member 12 so that surgical instruments (not shown) can be inserted into the lumen 15 of tubular member 12 to access the body cavity below (see FIG. 3C). The pneumostasis valve 13 prevents loss of gas by automatically closing access to the tubular member 12 when surgical instruments are being switched.

In further embodiments of the device of the present invention, FIGS. 4A and 4B show an access assembly 10B and 10C (with the obturator 11 removed) capable of forming a distal expanded anchor 30 and an intermediate expanded anchor 50. Having two expanded anchors integrated onto the access assembly reduces the need for extra parts like the non-expanding anchor 40 and results in a more compact, integrated device.

The embodiment of FIG. 4A shows an access assembly 10B (with obturator 11 removed) comprising a sleeve 16 having distal expandable region 19 and an intermediate expandable region 51. When sleeve 16 is advanced towards the distal end of the tubular member 12, both expandable regions 19 and 51 expand radially to form distal anchor 30 and intermediate anchor 50, respectively. The expansion of these regions are coupled, as either both regions expand or neither expand. Again the distal end of expandable region 19 is connected to the distal end of tubular member 12. Preferably, the maximum expanded outer diameter of the intermediate anchor will be in the range from about 10 mm to 50 mm.

In the embodiment of FIG. 4B, an access assembly 10C (shown with obturator 11 removed) has expandable regions 19 and 60 that can expand independently of the other (i.e. decoupled). The assembly 10C has a second sleeve 61 that is slidably disposed over first sleeve 16 in a coaxial manner and has an activation handle 62. The second sleeve 61 is preferably fitted over the non-expanding portion 18 of the first sleeve 16. This decoupled configuration allows for sequential, as well as simultaneous, deployment of anchors 30 and 50. This may result in a better seal as each anchor may be independently adjusted to conform to the surface against which it seals. The expansion of region 60, which is located at the distal end of sleeve 61, is independent of any radial expansion of distal expandable region 19. A distal end of second sleeve 61 is fixedly attached to the nonexpandable region 18 of sleeve 16. This prevents second sleeve 61 from falling off of the sleeve 16 and provides a fixed point against which region 60 axially compresses. The embodiment of FIG. 4B allows for decoupled activation of intermediate anchor 50 and distal anchor 30.

Figure 5B:
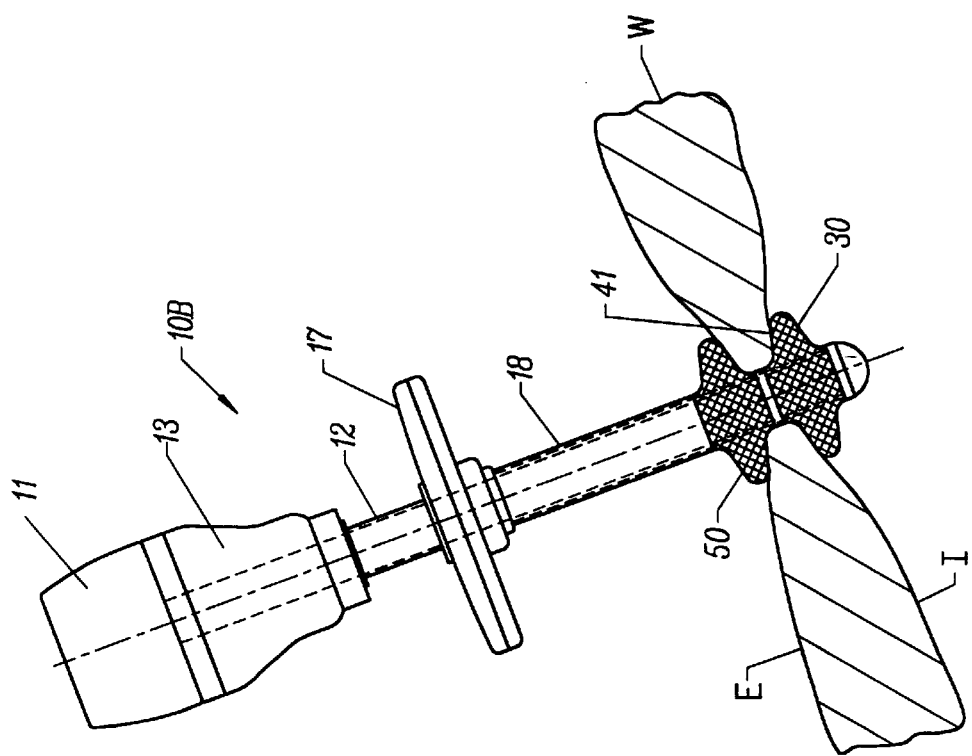
FIGS. 5A–5B depicts a method of the present invention using the assembly of FIG. 4A.
Figure 5A:
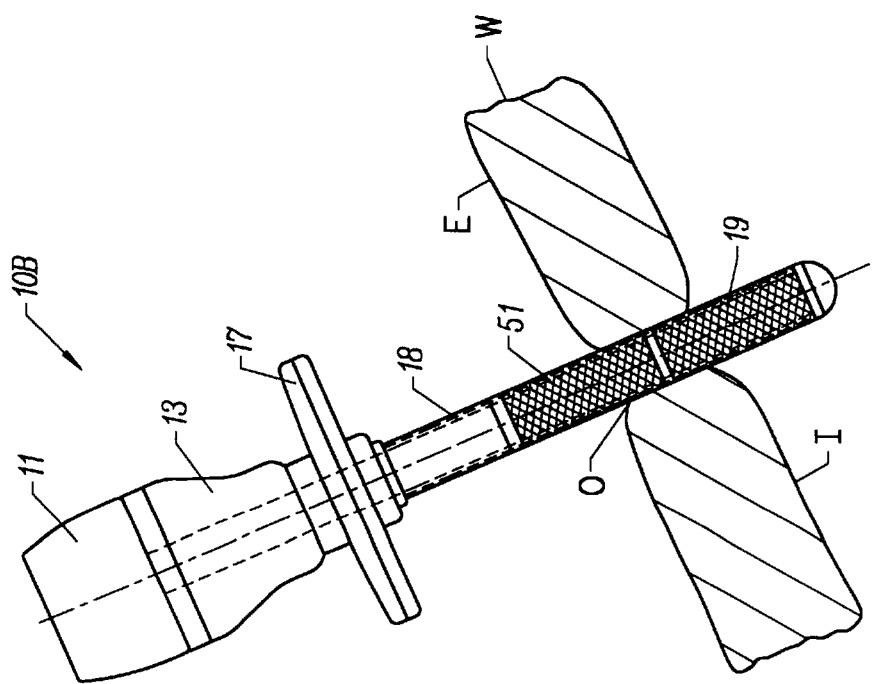

Referring to FIGS. 5A–5B, a further method of the present invention is depicted using the assembly of FIG. 4A having the coupled anchors. After abdominal wall W has been penetrated, the assembly 10B is inserted into the opening O to a depth sufficient to have the distal anchor 30 seal on an interior surface I of the wall. The position of the assembly 10B will also allow the intermediate expanded anchor 50 to form a seal on the exterior surface E of the abdominal wall W. The sleeve 16 is translated axially towards the distal end 21 of the assembly, causing both expandable regions 19 and 60 to simultaneous form anchors 30 and 50. The intermediate anchor 50 will preferably have a conical configuration which diverges in the proximal direction so that the expanded anchors 30 and 50 when brought together define a neck 41 having opposed tapered walls. After the seal is formed, the obturator 11 is removed from lumen 15 of the tubular member 12 (not shown).

FIGS. 6A–6D depict a still further method of the present invention using the access assembly of FIG. 4B having decoupled anchors 30 and 50. The assembly 10C is inserted through an opening 0 in the abdominal wall W. Then either the distal or intermediate expandable regions may be compressed to form an anchor. Preferably, the distal region will be expanded first. This allows anchor 30 to be retracted against the interior surface I of the wall W to ensure a conforming seal (see FIG. 6B). The seal, however, is not so tight as to cause trauma to the abdominal wall. Both the first and second sleeves 16 and 61 are distally translated in FIG. 6C, causing expanded anchors 30 and 50 to clamp on both sides of the abdominal wall W. FIG. 6D shows the obturator 11, used to facilitate entry of the assembly 10C into the opening, removed from lumen 15 to allow surgical instruments access though the tubular member 12 to the body cavity below.

To more suitably handle changing conditions that may be encountered during a surgical procedure, it is further desirable that the depth or length of the access assembly 10, protruding beyond the expandable anchor 30 and into the body cavity, be adjustable. This may be accomplished through a variety of methods, so long as expandable anchor 30 has a secured point of reference against which the anchor 30 may compress against, once the depth or length of the assembly extending into the cavity has been adjusted.

Figure 7A:
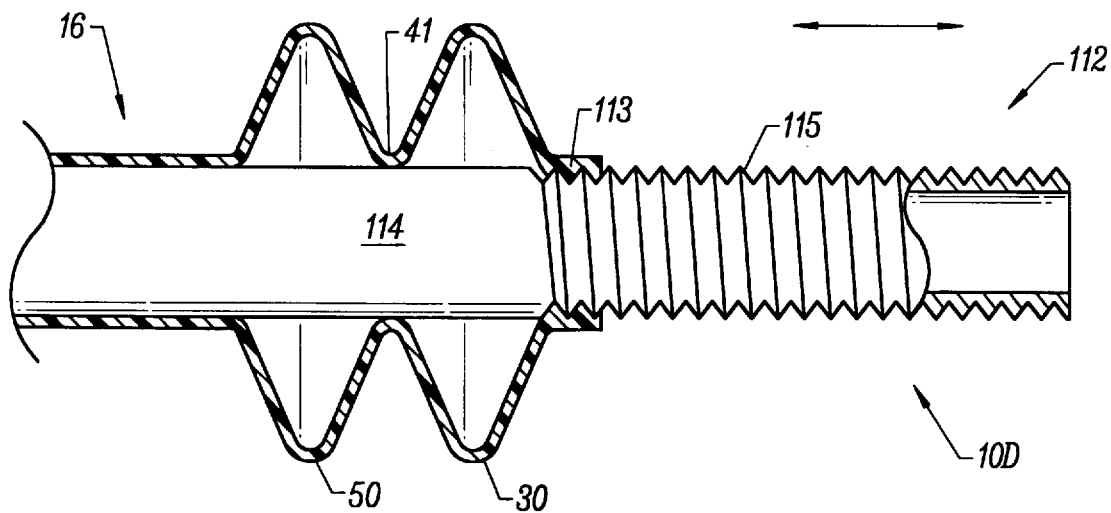
FIG. 7A illustrates an enlarged cross-section of the distal end of the assembly fitted with a threaded tubular member.

For example, FIG. 7A depicts the distal end of an assembly 10D with a threaded tubular member 112 which can be rotated to extend further into the abdominal cavity (as indicated by the arrows) while the anchors 30 and 50 clamp about the opening O (not shown) in the abdomen. The member 112 mates with threaded end 113 on first sleeve 16 to provide axial resistance for the anchor 30, while still allowing for the threaded tubular member 112 to be extended or retracted through rotational motion. The threaded tubular member 112 would likely be manipulable or rotatable from the proximal end of the assembly 10D so that adjustments can be made while the assembly is clamped around the abdominal wall. As shown by unthreaded region 114, the threads 115 of the member 112 do not necessarily extend along the entire outer surface of the member 112.

Figure 7B:
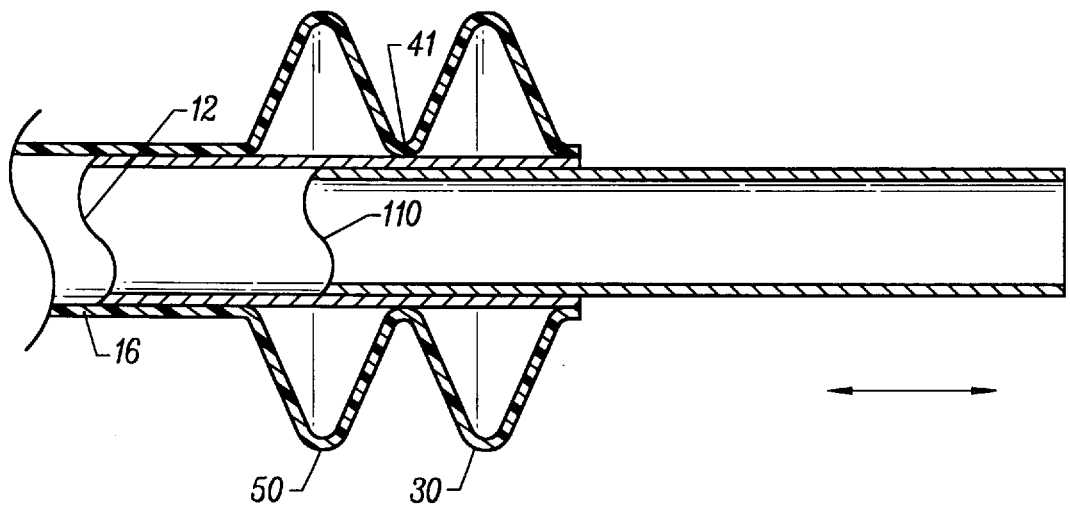
FIG. 7B shows an enlarged cross-section of the distal end of the assembly having a cannula concentrically disposed within the tubular member.

FIG. 7B depicts an alternative embodiment for varying the depth of which the assembly 10 extends into the abdominal cavity. A cannula 120 is added to the assembly 10 and is slidably disposed concentrically within the tubular member 12. The cannula 120 translates axially (as indicated by arrows) to extend or retract from the body cavity. Preferably, the cannula 120 would extend along the entire length of tubular member 12 and be manipulable from a proximal end of the assembly 10. This particular embodiment of the present invention has the advantage of not requiring significant modification of the assembly 10. A still further embodiment of the invention may use a collet mechanism or ratcheting-type mechanism (not shown) on a distal end of anchor 30 to lock and unlock about tubular member 12 as the length which the assembly 10 protrudes into the body cavity is adjusted. This allows for axial adjustability while providing the necessary secured point of reference for anchor 30 to compress against, once length adjustments have been completed.

Although the foregoing invention has been described in detail for purposes of clarity of understanding, it will be obvious that certain modifications may be practiced within the scope of the appended claims.

What is claimed is:

1. An abdominal access assembly comprising:
   a tubular member having a proximal end, a distal end, and a lumen therethrough;
   a first sleeve disposed coaxially over the tubular member, said sleeve having:
   (a) a distal radially expandable region,
   (b) a proximal non-expandable region,
   wherein the sleeve is shiftable over the tubular member from an axially elongated configuration to an axially shortened configuration to radially expand the distal region, wherein the expanded distal region provides a structure which is capable of sealing against an internal surface of an abdominal wall;

a pneumostasis valve attached to the proximal end of the tubular member; and an obturator removably receivable in the lumen of the tubular member.

2. An assembly of claim 1 further comprising a non-expandable sealing anchor slidably mounted over the proximal non-expandable region of the sleeve, wherein the non-expandable sealing anchor can be advanced toward the radially expanded, expandable region to clamp a patient's abdominal tissue.

3. An assembly of claim 2 wherein the sealing anchor has a conical configuration which diverges in the proximal direction so that the expanded distal, expandable region and the sealing anchor when brought together define a neck having opposed tapered walls.

4. An assembly of claim 1 wherein:

said sleeve has an intermediate radially expandable region;

said sleeve is shiftable over the tubular member between an axially elongated configuration where both the distal and the intermediate regions are unexpanded and an axially shortened configuration where both the distal and the intermediate regions are radially expanded.

5. An assembly of claim 1 further comprising:

a second sleeve disposed coaxially over the proximal non-expandable region of said first sleeve, said second sleeve having a distal, a proximal end, and an intermediate radially expandable region;

said intermediate region attached to the distal end of the second sleeve, wherein the second sleeve is shiftable over said first sleeve between an axially elongated configuration where the intermediate region is unexpanded and an axially shortened configuration where the intermediate region is radially expanded.

6. An assembly of claim 1 wherein the distal expandable region comprises a non-distensible imperforate cylinder.

7. An assembly of claim 1 wherein the distal expandable region comprises a radially expandable mesh covered with an elastomer sheath.

8. An assembly of claim 1 wherein the tubular member has a length in the range from 5 to 15 cm and an outside diameter in the range from 4 to 20 mm.

9. An assembly of claim 1 sized to be received into the umbilicus of the patient.

10. An assembly of claim 1 wherein a length of said tubular member extends beyond the distal end of the first sleeve, said length being adjustable in the axial direction.

11. An assembly of claim 1 further comprising a cannula contained concentrically within said tubular member, said cannula being slidably disposed within said member.

12. A method for providing access to a patient's abdomen, said method comprising:

introducing a tubular body through a penetration in the patient's abdomen;

axially compressing a radially expandable member mounted on the tubular body to radially expand the member to provide a seal against the internal surface of an abdominal wall; and insufflating the abdomen with a gas, wherein the seal inhibits loss of the gas through the penetration.

13. A method of claim 12 further comprising axially advancing a proximal anchor on said tubular body to clamp against the abdominal wall.

14. A method of claim 12 wherein the axially compressing step comprises compressing an intermediate radially expandable member and a distal radially expandable member to radially expand both said members to clamp an abdominal wall therebetween, said distal member providing a seal against the internal surface of an abdominal wall.

15. A method of claim 14 wherein the distal and intermediate radially expandable members are axially compressed simultaneously.

16. A method of claim 14 wherein the distal and intermediate radially expandable members are axially compressed sequentially.

17. A method of claim 12 wherein the penetration occurs through the patient's umbilicus.

18. A method of claim 12 wherein:

said tubular body has a lumen therethrough, said lumen contains a removably receivable blunt obturator.

19. A method of claim 18 further comprising removing said blunt obturator from the lumen after introducing the tubular body through the penetration.

20. A method for providing access through a patient's abdominal wall comprising:

introducing a tubular body through a penetration in the patient's abdominal wall;

radially expanding a first radially expandable member mounted on said tubular body;

radially expanding a second radially expandable member, mounted proximal of the first member on said tubular body, by axially compressing said second member;

said expandable members clamping the abdominal wall therebetween.

21. An improved cannula and obturator assembly of the type comprising (1) a cannula having a pneumostasis valve, a distal seal, and a proximal clamp and (2) an obturator removably receivable in a lumen of the cannula, the improvement comprising:

a non-distensible imperforate cylinder disposed over a distal portion of the cannula, wherein said cylinder expands radially when axially shortened to provide the distal seal.

* * * * *